US009532908B2

(12) United States Patent
Wade et al.

(10) Patent No.: US 9,532,908 B2
(45) Date of Patent: Jan. 3, 2017

(54) TEXTURED LAMINATE SURFACE, ABSORBENT ARTICLES WITH TEXTURED LAMINATE STRUCTURE, AND FOR MANUFACTURING

(71) Applicant: The Procter & Gamble Company, Cincinnati, OH (US)

(72) Inventors: Sarah Marie Wade, Mount Healthy, OH (US); Masaharu Nishikawa, Cincinnati, OH (US); Kaoru Ishihara, West Chester, OH (US); Tina Marie Glahn, West Chester, OH (US); Gary Dean Lavon, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 405 days.

(21) Appl. No.: 14/032,595

(22) Filed: Sep. 20, 2013

(65) Prior Publication Data

US 2015/0088088 A1   Mar. 26, 2015

(51) Int. Cl.
*A61F 13/15* (2006.01)
*A61F 13/49* (2006.01)
*A61F 13/72* (2006.01)

(52) U.S. Cl.
CPC ... *A61F 13/49012* (2013.01); *A61F 13/15593* (2013.01); *A61F 13/4902* (2013.01); *A61F 13/49011* (2013.01); *A61F 13/72* (2013.01); *A61F 13/49007* (2013.01); *A61F 13/49014* (2013.01); *A61F 13/49015* (2013.01); *A61F 2013/49022* (2013.01); *A61F 2013/49023* (2013.01); *A61F 2013/49025* (2013.01); *A61F 2013/49026* (2013.01);

(Continued)

(58) Field of Classification Search
CPC ............ A61F 13/49007; A61F 13/4902; A61F 13/49014; A61F 13/49015; A61F 2013/49022; A61F 2013/49026; A61F 2013/29023
USPC ...... 604/396, 385.24, 385.27, 385.25, 385.36
See application file for complete search history.

(56) References Cited

U.S. PATENT DOCUMENTS

| 4,342,314 A | 8/1982 | Radel et al. |
| 4,710,189 A | 12/1987 | Lash |
| 4,781,966 A | 11/1988 | Taylor |

(Continued)

OTHER PUBLICATIONS

PCT International Search Report, mailed Nov. 14, 2014 (10 pages).

*Primary Examiner* — Jacqueline Stephens
(74) *Attorney, Agent, or Firm* — William E. Gallagher

(57) ABSTRACT

A textured laminate structure and absorbent articles having a component formed of the textured laminate structure are disclosed. The textured laminate structure may have a first layer formed of a nonwoven web having a preexisting pattern of first apertures therethrough, a second layer, and one or more elastic members disposed between the first and second layers in a prestrained condition. The laminate structure may be discontinuously joined or bonded such that the first layer is joined or bonded to the structure in first portions and unjoined or unbonded to the structure in second portions. The structure provides a stretch laminate with tactilely and visually interesting features, and may be used to form components of a disposable absorbent article such as a side panel thereof.

18 Claims, 12 Drawing Sheets

(52) U.S. Cl.
CPC .............. *Y10T 428/24298* (2015.01); *Y10T 428/24314* (2015.01); *Y10T 428/24331* (2015.01)

(56) References Cited

U.S. PATENT DOCUMENTS

| | | | |
|---|---|---|---|
| 4,847,134 | A | 7/1989 | Fahrenkrug et al. |
| 5,151,092 | A * | 9/1992 | Buell ............... A61F 13/15593 604/358 |
| 5,576,090 | A | 11/1996 | Suzuki |
| 5,629,097 | A | 5/1997 | McCann |
| 5,658,639 | A | 8/1997 | Curro et al. |
| 5,714,107 | A | 2/1998 | Levy et al. |
| 5,763,041 | A * | 6/1998 | Leak ............... A61F 13/539 24/447 |
| 5,916,661 | A | 6/1999 | Benson et al. |
| 6,632,385 | B2 | 10/2003 | Kauschke et al. |
| 6,645,569 | B2 | 11/2003 | Cramer et al. |
| 6,803,103 | B2 | 10/2004 | Kauschke et al. |
| 6,863,933 | B2 | 3/2005 | Cramer et al. |
| 7,112,621 | B2 | 9/2006 | Rohrbaugh et al. |
| 7,858,544 | B2 | 12/2010 | Turi et al. |
| 8,186,296 | B2 | 5/2012 | Brown et al. |
| 8,445,744 | B2 | 5/2013 | Autran et al. |
| 2005/0008839 | A1 | 1/2005 | Cramer et al. |
| 2011/0282313 | A1 | 11/2011 | Lu et al. |
| 2011/0319853 | A1 | 12/2011 | Yamashita et al. |
| 2013/0211355 | A1 | 8/2013 | Nishikawa et al. |

* cited by examiner

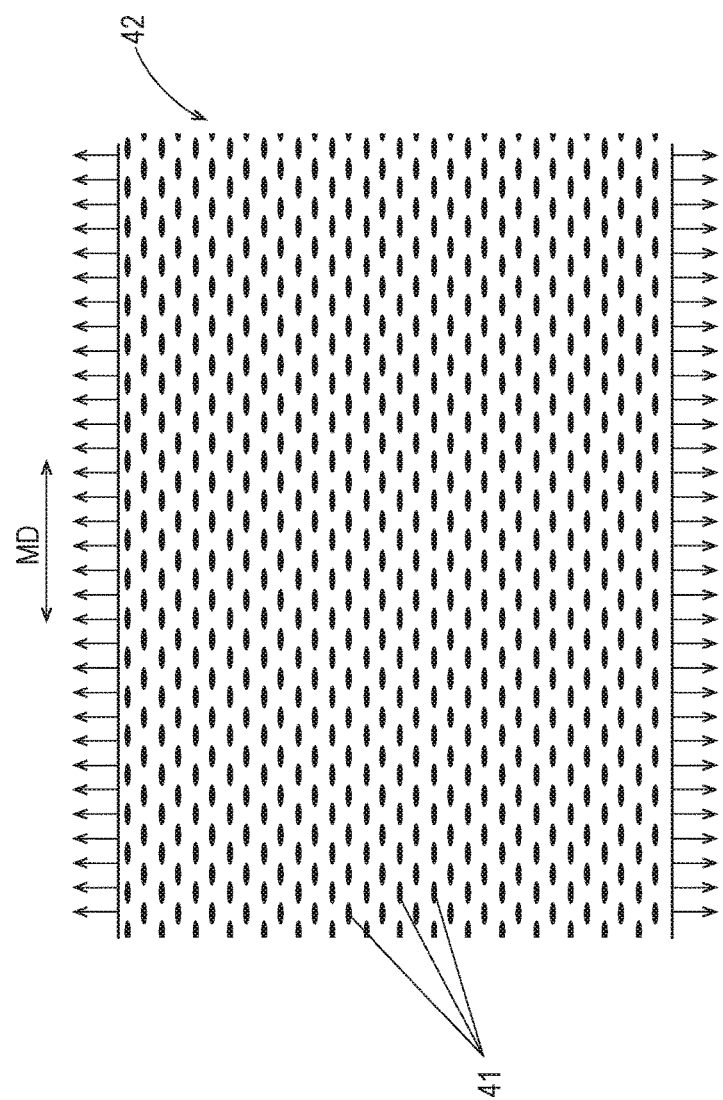

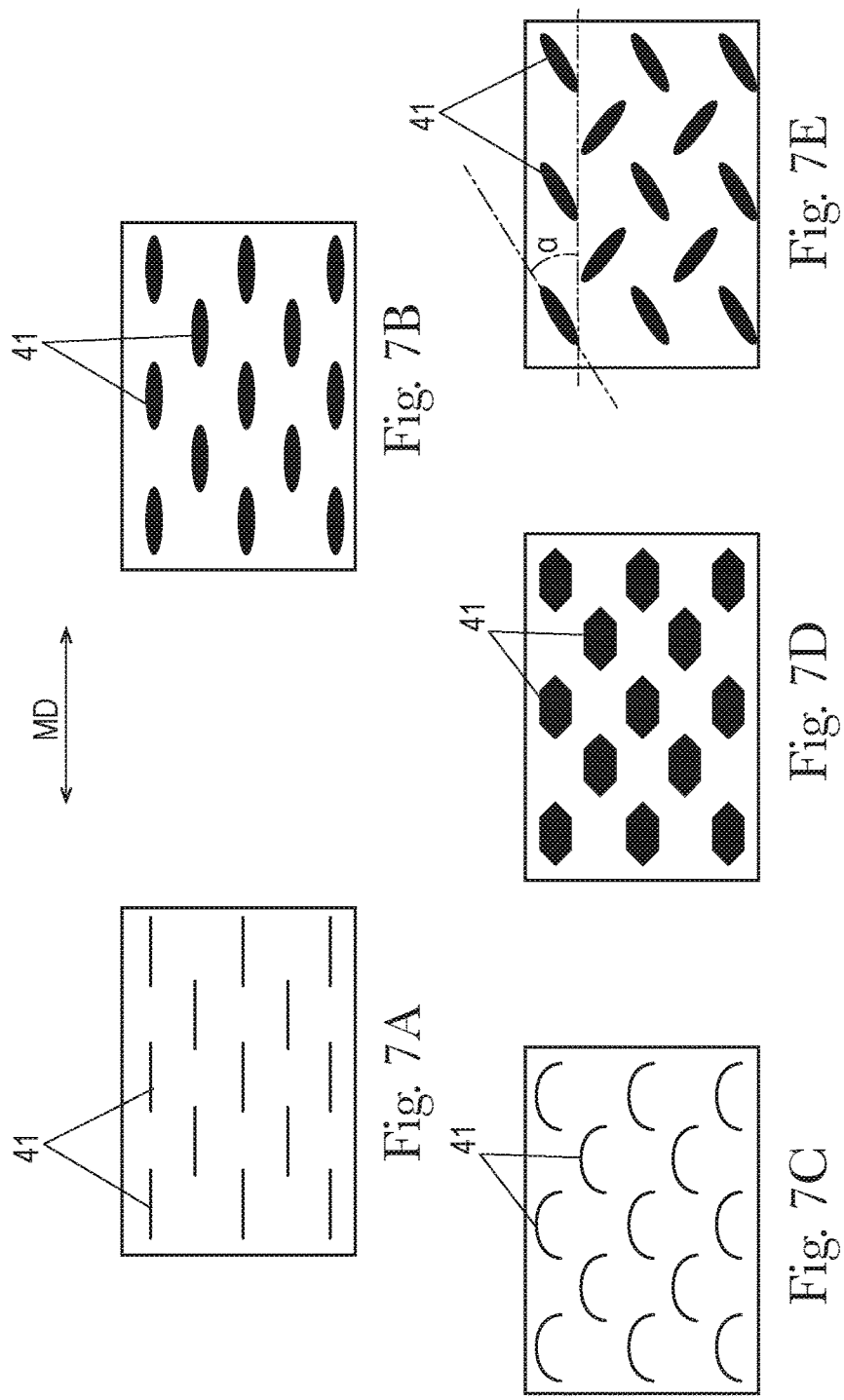

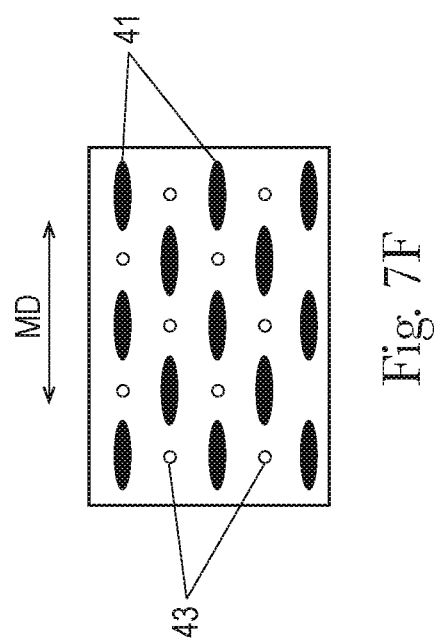

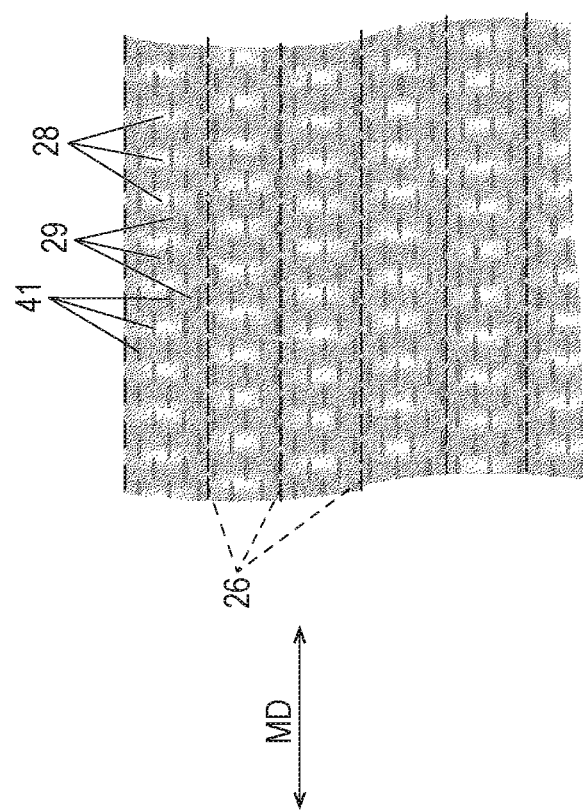

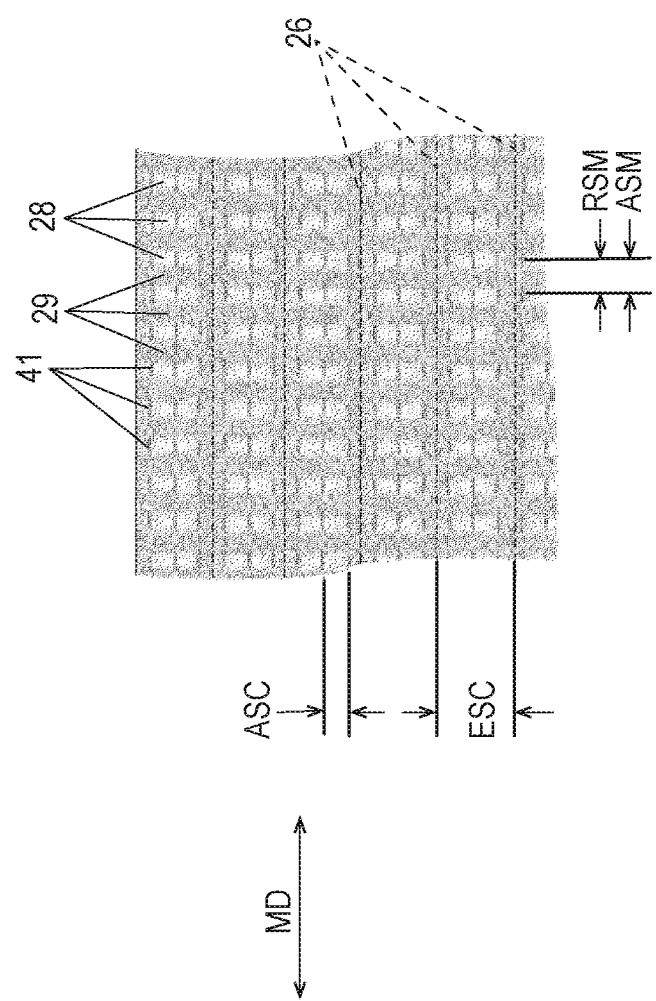

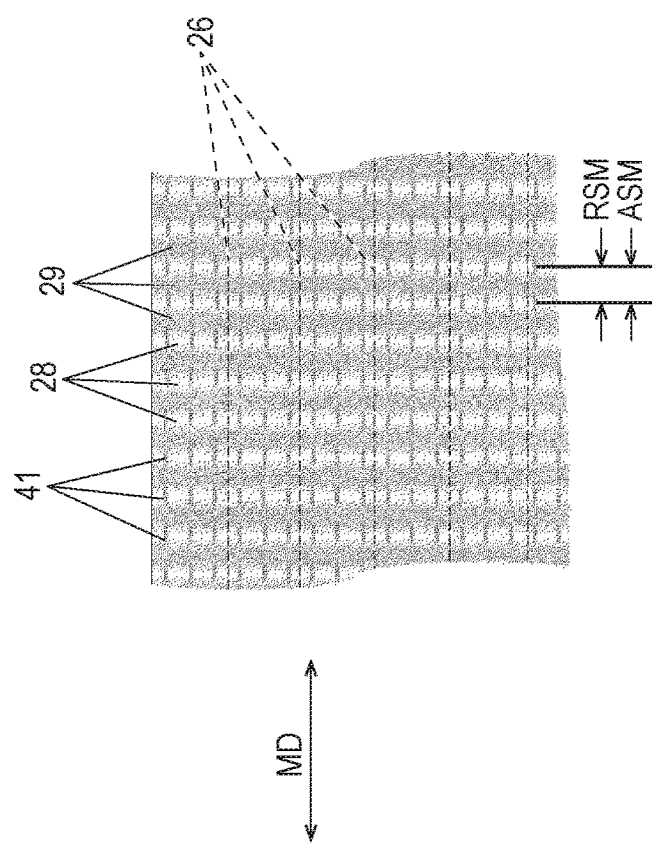

TEXTURED LAMINATE SURFACE, ABSORBENT ARTICLES WITH TEXTURED LAMINATE STRUCTURE, AND FOR MANUFACTURING

BACKGROUND OF THE INVENTION

In order to maintain or grow their market share, manufacturers of disposable absorbent articles such as disposable diapers and absorbent pants must continue to discover and develop improvements to materials, components and features that affect aspects such as containment, absorbency, comfort, fit and appearance. Absorbent pants are manufactured in smaller sizes to be used as, e.g., pull-on diapers and toilet training pants for young children, and in larger sizes to be used as, e.g., undergarments for persons suffering from incontinence.

A particular type of absorbent pant design currently marketed is sometimes called the "balloon" pant. The balloon pant design usually includes a central absorbent chassis and an elastic belt. The elastic belt is usually relatively wide (in the longitudinal direction) and elastically stretchable in the lateral direction. It entirely encircles the wearer's waist, and thereby covers a relatively large amount of the wearer's skin, and also makes up a relatively large portion of the visible outside surfaces of the pant. The central chassis portion is typically joined to the inside of the belt in the front, wraps under the wearer's lower torso between the legs, and is joined to the inside of the belt in the rear. The belt is often formed of two layers of nonwoven web sandwiching one or more elastic members such as a plurality of laterally-oriented strands or strips of elastomeric material, or a section of elastomeric film or elastomeric nonwoven. It is common among such designs that, in manufacture, the elastic member(s) are sandwiched between the nonwoven web layers in a strained condition. Upon completion of manufacture and allowance of the belt with sandwiched elastic member(s) to assume a relaxed condition, the elastic member(s) contract laterally toward their unstrained lengths. This causes the nonwoven web layers to form gathers that take the form of visible rugosities in the belt. It is believed that some consumers find the rugosities attractive because they present a textured, plush, frilly and/or soft appearance and feel, and also provide a visible indication of stretchability and comfortableness.

The balloon pant design provides for certain efficiencies in manufacture, and it is believed that the design may gain popularity. Consequently, any improvement in components such as the belt that enhance its appearance and functionality may give the manufacturer thereof an advantage.

BRIEF DESCRIPTION OF THE DRAWINGS

FIG. 6B is a plan view of a portion of the nonwoven web of FIG. 6A having a pattern of apertures following cross direction incremental stretching.

FIGS. 7A-7F are plan views of examples of apertures in a nonwoven web and shapes defined thereby.

FIG. 8A is a schematic, close-up plan view of a portion of an example of a belt wherein a nonwoven web component thereof has a pattern of apertures.

FIG. 8B is a schematic, close-up plan view of a portion of another example of a belt wherein a nonwoven web component thereof has a pattern of apertures.

FIG. 8C is a schematic, close-up plan view of a portion of another example of a belt wherein a nonwoven web component thereof has a pattern of apertures.

DETAILED DESCRIPTION OF THE INVENTION

Figure 1A:
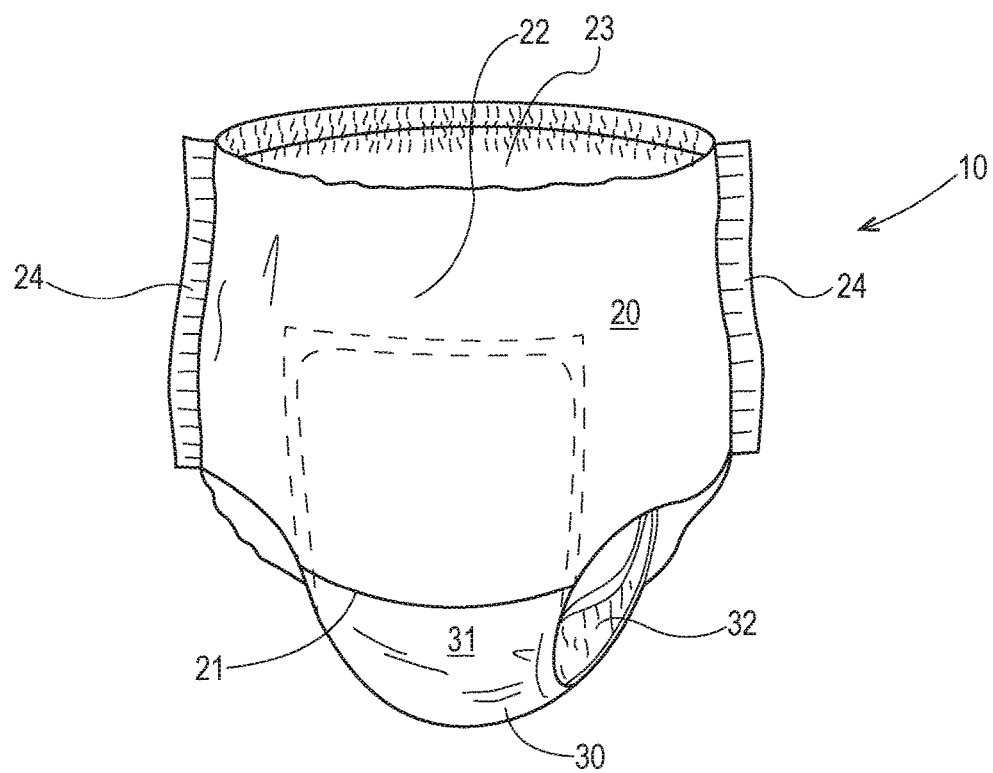
FIG. 1A is a perspective view of one example of a balloon pant.

"Cross direction" (CD)—with respect to the making of a nonwoven web material, the nonwoven material itself, a laminate thereof, or an article in which the material is a component, refers to the direction along the material substantially perpendicular to the direction of forward travel of the material through the manufacturing line in which the material and/or article is manufactured.

Throughout the present description, a material or composite of materials is considered to be "elastic" or "elastomeric" if, when a biasing force is applied to the material, the material or composite can be extended to an elongated length of at least 150% of its original relaxed length (i.e. can extend at least 50%), without rupture or breakage which substantially damages the material or composite, and when the force is removed from the material or composite, the material or composite recovers at least 40% of such elongation. In various examples, when the force is removed from an elastically extensible material, the material or composite may recover at least 60% or even at least 80% of its elongation.

"Film" means a skin-like or membrane-like layer of material formed of one or more polymers, which does not have a form consisting predominately of a web-like structure of consolidated polymer fibers and/or other fibers.

"Lateral"—with respect to a pant and its wearer, refers to the direction generally perpendicular with the wearer's standing height, or the horizontal direction when the wearer is standing.

"Longitudinal"—with respect to a pant and its wearer, refers to the direction generally parallel with the wearer's standing height, or the vertical direction when the wearer is standing. "Longitudinal" is also the direction generally parallel to a line extending from the midpoint of the front waist edge to the midpoint of the rear waist edge.

"Machine direction" (MD)—with respect to the making of a nonwoven web material, the nonwoven material itself, or a laminate thereof, refers to the direction along the material or laminate substantially parallel to the direction of forward travel of the material or laminate through the manufacturing line in which the material or laminate is manufactured.

"Machine direction bias," with respect to the fibers forming a nonwoven web, means that a majority of the fibers, as situated in the web and unstretched, have lengths with machine direction vector components that are greater than their cross direction vector components.

A "nonwoven" is a manufactured sheet or web of directionally or randomly oriented fibers which are first formed into a batt and then consolidated and bonded together by friction, cohesion, adhesion or one or more patterns of bonds and bond impressions created through localized compression and/or application of pressure, heat, ultrasonic or heating energy, or a combination thereof. The term does not include fabrics which are woven, knitted, or stitch-bonded with yarns or filaments. The fibers may be of natural and/or man-made origin and may be staple and/or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes including but not limited to meltblowing, spunbonding, spunmelting, solvent spinning, electrospinning, carding, film fibrillation, melt-film fibrillation, airlaying, dry-laying, wetlaying with staple fibers, and combinations of these processes as known in the art. The basis weight of nonwoven fabrics is usually expressed in grams per square meter (gsm).

"Preexisting," with respect to a pattern of apertures on a nonwoven web, the nonwoven web forming a layer of a laminate, means that the pattern of apertures was formed on the nonwoven web prior to the incorporation of the nonwoven web into the laminate.

"Z-direction," with respect to a web, means generally orthogonal or perpendicular to the plane approximated by the web along the machine and cross direction dimensions.

Although examples of the structure of the invention are described herein as used to form the belt of a balloon-type absorbent pant, it will be appreciated that examples may be used to form other components of pants, diapers, other wearable articles, and other products as well.

Figure 1B:
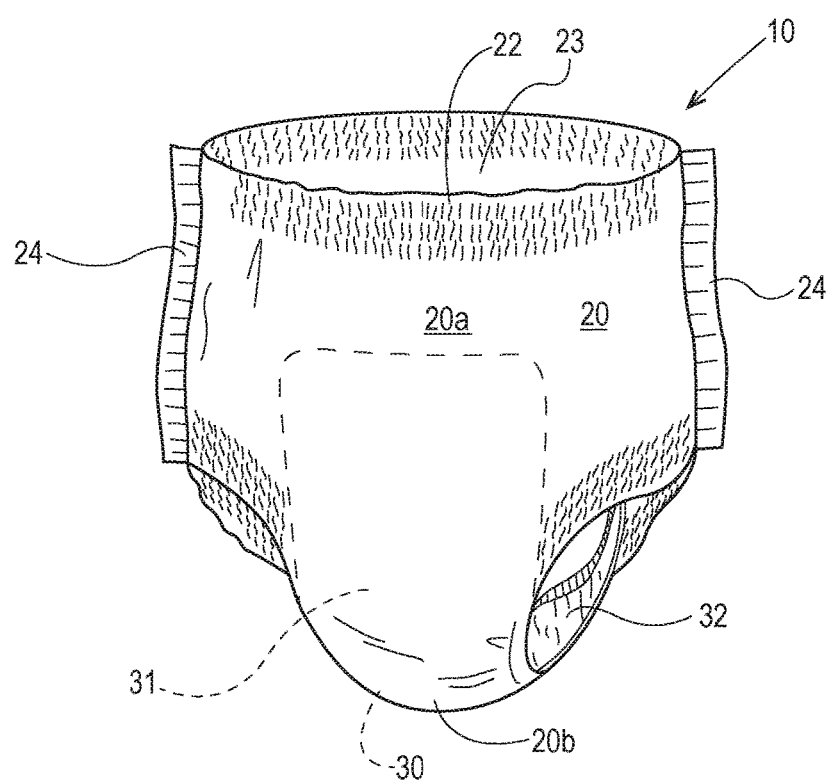
FIG. 1B is a perspective view of another example of a balloon pant.

FIGS. 1A and 1B depict examples of balloon-type absorbent pants 10. The structure may include a belt 20 and a central chassis 30. Central chassis 30 may include any combination of components found in disposable diapers and absorbent pants, including but not limited to a liquid impermeable backsheet 31, a liquid permeable topsheet (not shown), an absorbent core structure (not shown), and elasticized barrier cuffs 32. Examples and descriptions of components and configurations of a central chassis may be found in U.S. patent application Ser. No. 13/764,945, wherein the chassis described includes components and features that may be included in central chassis 30.

In the example shown in FIG. 1A, belt 20 stops short of the crotch region 12 of the pant, at lower edge 21. In the example shown in FIG. 1B, belt 20 is part of an outer structure that includes a belt portion 20a encircling the wearer's waist, an outer wrap portion 20b that overlies the central chassis to the outside thereof and wraps thereabout through the crotch region. The outer wrap portion 20b may be formed of a layer of nonwoven web, which also serves as the outer layer of the belt portion 20a. The belt may have front and rear portions 22, 23, which are joined together at seams 24.

Figure 2:
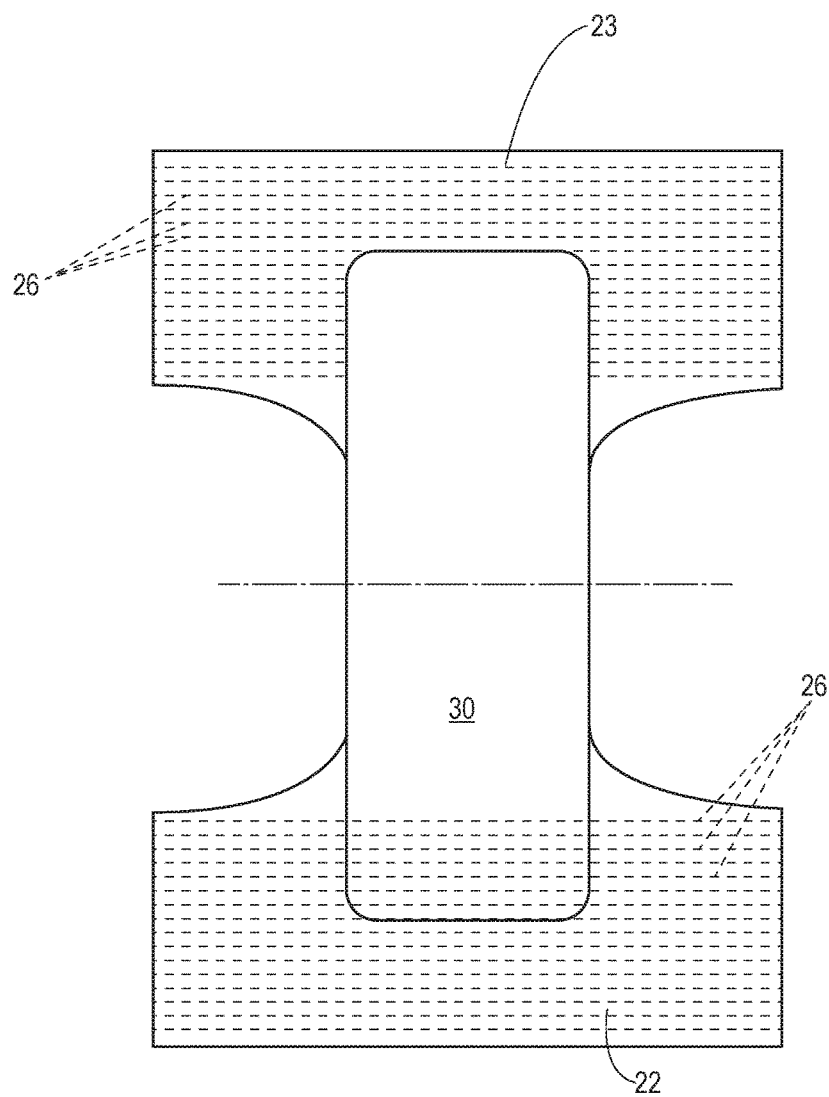
FIG. 2 is a schematic plan view of a balloon pant precursor structure, prior to joining of the front and rear sections of the belt.

FIG. 2 schematically depicts a structure that is the precursor to a pant such as depicted in FIG. 1B, prior to joining of front and rear portions 22, 23 at seams 24 as depicted in FIGS. 1A and 1B. Central chassis 30 overlies front and rear portions 22, 23 to the inside thereof.

Figure 3:
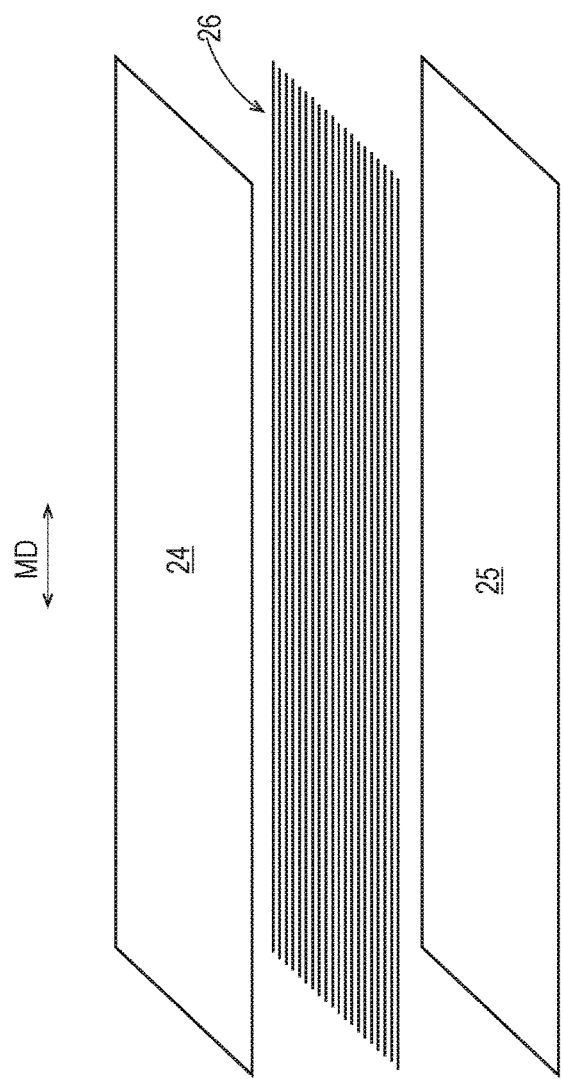
FIG. 3 is a schematic, exploded perspective view of components of a belt.
Figure 4:
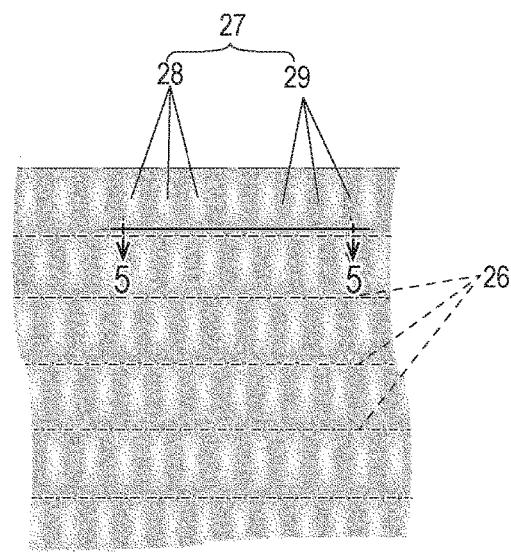
FIG. 4 is a schematic, close-up plan view of a portion of a belt.
Figure 5:
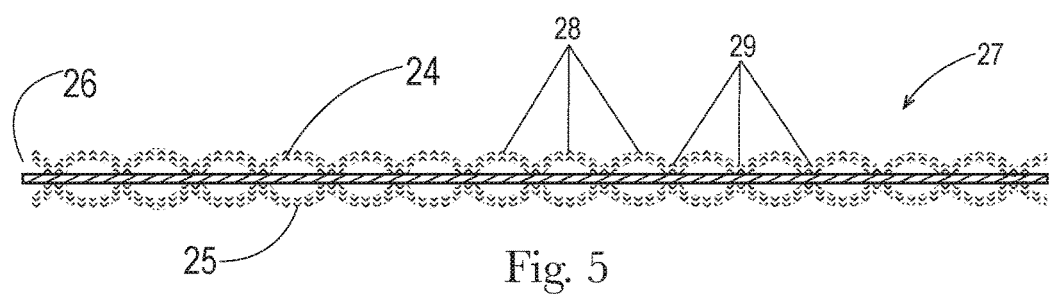
FIG. 5 is a schematic cross section of the portion of the belt shown in FIG. 4.

Referring to FIGS. 3-5, belt 20 may be formed of layers of nonwoven web 24, 25, which respectively form inner and outer layers of the belt. Suitable nonwoven web materials that may be useful in the present invention also include, but are not limited to spunbond, spunlaid, meltblown, spunmelt, solvent-spun, electrospun, carded, film fibrillated, melt-film fibrillated, air-laid, dry-laid, wet-laid staple fibers, and other and other nonwoven web materials formed in part or in whole of polymer fibers, as known in the art. The nonwoven web may be formed predominately of polymeric fibers. In some examples, suitable non-woven fiber materials may include, but are not limited to polymeric materials such as polyolefins, polyesters, polyamide, or specifically, polypropylene (PP), polyethylene (PE), poly-lactic acid (PLA), polyethylene terephthalate (PET) and/or blends thereof. In some examples, the fibers may be formed of PP/PE blends such as described in U.S. Pat. No. 5,266,392 to Land, the disclosure of which is incorporated by reference herein. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. No. 6,645,569 to Cramer et al.; U.S. Pat. No. 6,863,933 to Cramer et al.; and U.S. Pat. No. 7,112,621 to Rohrbaugh et al.; and in co-pending U.S. patent application Ser. Nos. 10/338,603 and 10/338,610 by Cramer et al.; and Ser. No. 13/005,237 by Lu et al., the disclosures of which are incorporated by reference herein.

The individual fibers may be monocomponent or multicomponent. The multicomponent fibers may be bicomponent, such as in a core-and-sheath or side-by-side arrangement. Often, the individual components comprise polyolefins such as polypropylene or polyethylene, or their copolymers, polyesters, thermoplastic polysaccharides or other biopolymers.

According to one example, the nonwoven may comprise a material that provides good recovery when external pressure is applied and removed. Further, according to one example, the nonwoven may comprise a blend of different fibers selected, for example from the types of polymeric fibers described above. In some embodiments, at least a portion of the fibers may exhibit a spiral curl which has a helical shape. According to one example, the fibers may include bicomponent fibers, which are individual fibers each comprising different materials, usually a first and a second polymeric material. It is believed that the use of side-by-side bi-component fibers is beneficial for imparting a spiral curl to the fibers.

In order to enhance softness perceptions of the laminate, nonwovens may be treated by hydrojet impingement, which may also be known as hydroenhancement, hydroentanglement or hydroengorgement. Such nonwovens and processes are described in, for example, U.S. Pat. Nos. 6,632,385 and 6,803,103, and U.S. Pat. App. Pub. No. 2006/0057921, the disclosures of which are incorporated herein by reference.

Other examples of nonwoven web that may be useful in the present laminate may be an SMS web (spunbond-meltblown-spunbond web) made by Avgol Nonwovens LTD, Tel Aviv, Israel, under the designation XL-S70-26; a softband SSS (spunbond-spunbond-spunbond) web made by Pegas Nonwovens AS in Znojmo, Czech Republic, under the designation 18 XX 01 00 01 00 (where XX=the variable basis weight); an SSS web made by Gulsan Sentetik Dok San VE TIC AS, in Gaziantep, Turkey, under the designation SBXXF0YYY (where XX=the variable basis weight, and YYY=the variable cross direction width); an HESB (hydroenhanced spunbond) web made by First Quality Nonwovens Inc., in Hazelton, Pa., under the designation SEH2503XXX (where XXX=the variable cross direction width): and a bicomponent SS web.

A nonwoven web useful as a component to form one or both of layers 24, 25 may be pre-bonded, prior to aperturing as described below. A batt of fibers may be calendered and pre-bonded in a pattern, to consolidate the batt/fibers and create a pattern of bonds that adds tensile strength and dimensional stability, converting the batt of fibers to a coherent and useable nonwoven web material. The web may be imparted with a pattern of pre-bonding as described in, for example, U.S. Pat. No. 5,916,661 (pre-bonding in a pattern of "point calendered bonds 200 to form a coherent web structure") and co-pending U.S. application Ser. No. 13/893,405 (pattern of "primary fiber bonds"). The pre-bonding may consist of a pattern of thermal bonds, mechanical bonds or adhesive bonds, although in some circumstances thermal bonding may be preferred.

Layers of nonwoven web 24, 25 may sandwich one or more elastic members such as a plurality of strands 26 of an elastomeric material, such as an elastane (for example, LYCRA HYFIT fiber, a product of Invista, Wichita, Kans.). Layers of nonwoven web 25, 26 may be joined together about elastic strands 26 by adhesive deposited between the layers, by thermal bonds, by compression bonds, or by a combination thereof. In other examples, the one or more elastic members may be strips or a section of film formed of elastomeric material.

The elastomeric members can also be formed from various other materials, such as but not limited to, rubbers, styrene ethylbutylene styrene, styrene ethylene propylene styrene, styrene ethylene ethylene propylene styrene, styrene butadiene styrene, styrene isoprene styrene, polyolefin elastomers, elastomeric polyurethanes, and other elastomeric materials known in the art, and combinations thereof. In some embodiments, the elastic members can be extruded strand elastics with any number of strands (or filaments). The elastomeric members can have a decitex ranging from 50 to 2000, or any integer value for any decitex value in this range, or any range formed by any of these integer values. The elastomeric members may be in a form of film. Examples of films have been described extensively in prior patent applications (see, for example, U.S. Pat. App. Pub. No. 2010/0040826). The film may be created with a variety of resins combined in at least one of several sublayers, the latter providing different benefits to the film.

During manufacture of the belt structure, the elastic member such as elastic strands 26 may be strained lengthwise by a desired amount as they are being incorporated into the belt structure. Upon subsequent relaxation of the belt, the elastic member such as elastic strands 26 will contract toward their unstrained lengths. This causes the layers of nonwoven material 24, 25 to gather and form ruffles or rugosities 27 having ridges 28 and valleys 29 generally transverse to the lengths of the elastic strands 26.

It may be appreciated that the size(s) and shape(s) of the rugosities 27 will be affected, and may be manipulated, by design of the pattern of joined portions and/or bonding between the layers of nonwoven web 24, 25, with respect to each other and with respect to elastic strands 26. When joining and/or bonding is effected using adhesive deposited upon one or both layers 24, 25 prior to lamination, the adhesive may be deposited in a pattern. Examples of methods for applying patterned deposits of adhesive to a nonwoven web substrate to enable manufacture of an elasticized laminate are described in U.S. Pat. No. 8,186,296. The pattern selected may be effected by design of a correspondingly designed roller. The pattern of adhesive to be applied may be designed to affect the size(s) and shape(s) of the rugosities 27. The layers 24, 25 may be adhesively joined and/or bonded to each other at the locations of adhesive deposits, and remain unjoined or unbonded, or free, of each other at other locations, such that they may move and shift slightly relative each other as the laminate is moved and stretched, as during wear of the article. Similarly, when joining and/or bonding is effected using thermal calender bonding, the joining and/or bonding pattern may be designed to affect the size(s) and shapes of the rugosities 27.

Apertured topsheets have been included in absorbent articles of the type described herein. Creating apertures in nonwoven material used to form a topsheet enhances its ability to allow aqueous liquid exudates to pass therethrough. In some circumstances this may be desired because materials of which topsheets are often formed may include polymers (such as polyolefins) that are normally hydrophobic, and pores or passageways ordinarily present between the nonwoven fibers may be insufficiently large to allow aqueous liquids to pass therethrough at a desired rate because the material tends to repel aqueous liquid.

Figure 6A:
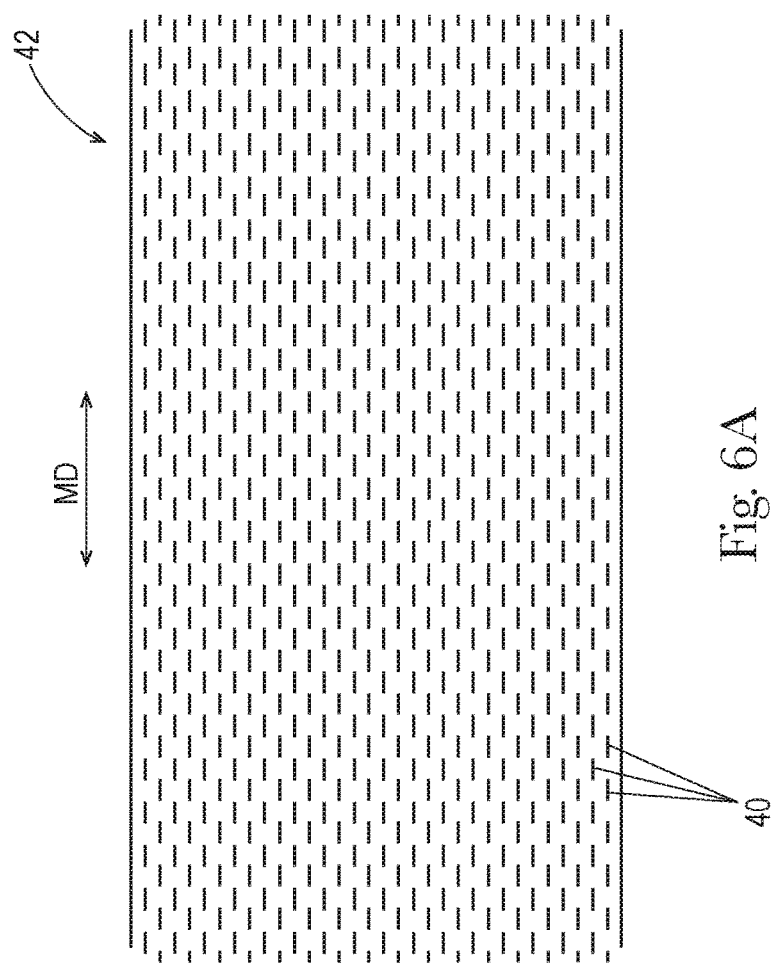
FIG. 6A is a plan view of a portion of nonwoven web having a pattern of rod-shaped bonds.

An example of a process for creating apertures in a pre-bonded nonwoven web to be used to form a topsheet is described in U.S. Pat. Nos. 5,916,661 and 5,629,097. This process involves rolling the pre-bonded nonwoven web through the nip between a pair of rollers, one of which bears a pattern of raised bonding protrusions, and supplying heating energy to heat the fibers beneath the protrusions in the nip. When appropriately controlled pressure and heating energy are provided at the nip, a pattern of suitable bonds or "weakened, melt-stabilized locations" having rod shapes or other shapes results. At the bond sites, the polymer fibers of the web are melted, compressed and thereby fused, such that the fused polymer material at the bond sites is relatively thin (in the z-direction) and frangible. Upon subsequent cross direction incremental stretching of the bonded nonwoven web as described in the above-cited patents, the material at the bond sites or "melt-stabilized locations" breaks and apertures open in a direction transverse to the long dimension of the rod shapes. For example, as depicted in FIG. 6A, a nonwoven web 42 may be thermal/calender bonded with a bonding pattern of rod shapes 40 having their long dimension oriented in the machine direction. Following such bonding, the web 42 may be subjected to an incremental stretching process to stretch the web in the cross direction, as suggested by the arrows in FIG. 6B. When the bonding process has been appropriately controlled to create relatively thin, frangible bond sites, this causes the rod-shaped bonds to break open, creating apertures 41 through the web. Advantageously, fibers of the nonwoven web along the edges of the apertures 41 are fused as a result of the bonding process. In comparison to a process in which apertures are simply punched or cut through the web without application of heating energy, the bonding/stretching process described in the above-cited patent does not cut the fibers, which can result in loose fibers and fraying about the edges of the punched or cut apertures. In contrast, the bonding/stretching process described herein tends not to create loose fibers, and provides more neatly defined edges about the apertures. Following incremental stretching, the web may be allowed to relax, which may cause the apertures to close to some extent, but they will still be present.

In another example, the web 42 may be bonded by compression bonding without the application of externally-produced or additional heating energy. Examples of suitable compression bonding systems utilizing rollers are described in, for example, U.S. Pat. Nos. 4,854,984 and 4,919,738. In these types of mechanisms, a first roller and second roller are arranged with their axes in parallel and urged together to form a nip. The first roller may have on its surface one or more bonding protrusions arranged in a pattern. The first roller and second roller may be urged together by one or more actuators such as bellows-type pneumatic actuators acting directly or indirectly on one or both of their axles, to provide and regulate compression, beneath the protrusions at the nip, of the web material as it passes therethrough, in the manner described in the aforementioned patents. A compression bonding mechanism such as, but not limited to, the mechanism described in the aforementioned patents, provides bonding of a nonwoven web material through rapid compression of superimposed fibers beneath the bonding protrusions, along the roller nip line. Without intending to be bound by theory, it is believed that rapid compression beneath the protrusions causes the respective materials to be rapidly deformed and partially expressed together from beneath the protrusions, to form structures of deformed, compressed and entangled fiber material beneath and/or around the protrusions. Welds or weld-like structures at or about the protrusions result. In some circumstances compression bonding provides advantages, including relative simplicity and cost effectiveness. It may reduce or eliminate the need for more complex bonding systems that require a system to supply externally produced or additional heating energy. Without intending to be bound by theory, it is believed that these advantages are substantially independent of variations in line speeds in at least some circumstances, including line speeds within currently known economically and technically feasible ranges for manufacture of disposable diapers and training pants. Following such creation of compression bonds, the web may be incrementally stretched to create apertures at the bond sites, in the manner taught by U.S. Pat. No. 5,916,661.

As noted, as suggested in U.S. Pat. No. 5,916,661, prior to aperturing, the nonwoven web may be pre-bonded with a relatively dense pattern of thermal/calender bonds. Following that, a pattern of apertures may simply be punched or cut through the web. A relatively dense pattern of bonding can serve to minimize loose cut fibers and fraying, and help maintain defined edges of apertures formed by cutting or punching.

It will be appreciated that the apertures created need not necessarily be rod-shaped. Other examples of shapes and patterns are described in co-pending provisional application Ser. No. 61/820,987. Also, as shown by the examples in FIGS. 7A-7C, the apertures may be rod-shaped, arc-shaped, other curved finite paths, circular, oval, elliptical or polygon, and any combinations thereof. It may be desired in some circumstances as suggested in the figures, however, that the longest dimension of a majority of the individual apertures 41 be oriented along the machine direction of the nonwoven web—particularly when the web or components of it are formed by processes that produce a machine direction bias in the fibers such as spunbonding or spunlaying processes. (For purposes herein, "oriented along the machine direction" means that the machine direction vector component of the longest dimension of an aperture is greater than the cross direction vector component.) Because of such fiber orientation, this reduces chances that sections of fibers between adjacent apertures along the machine direction will fray or tear away. At the same time, however, while it may be desired in some circumstances that the longest dimension of a majority of the apertures be oriented along the machine direction, it may also be desired that the longest dimension is not parallel with the machine direction. In one example, illustrated in FIG. 7E in which the apertures are elliptical or oval-shaped, it may be desired that their longest dimensions are oriented along angle(s) α between greater than 0 and less than 45 degrees of the machine direction. It will be appreciated that this may add to visual and actual texturing effects, by causing the material along the edges of the apertures to move in a more complex manner in the machine, cross and z-directions as the belt is stretched and moved as during wear. It will also be appreciated that the apertures may be arranged in varying patterns, such as but not limited evenly-spaced and aligned rows and columns, offset rows and columns, diagonal patterns, shaped patterns, etc.

Additionally, the pattern of the apertures may be substantially similar or identical to the pattern of the pre-bonds (if present), in one or more of machine-direction spacing, cross-direction spacing, aperture shape and aperture size. For example, referring to FIG. 7F, a pattern of pre-bonds 43 may have substantially similar machine and cross direction spacing as the pattern of apertures 41. Using respective patterns of pre-bonds and apertures that are substantially similar in one or more respects noted can help give the material a more uniform, orderly and/or coherent appearance, and may also help enhance tensile strength as compared with a web in which respective patterns of pre-bonds and apertures do not have such similarities.

Using a nonwoven web that has been apertured in the manner described above to form one or both of nonwoven web layers 24, 25, in a belt as described above, can provide attractive and interesting effects. The apertures and the material surrounding them interact with the contraction-induced rugosities in the web layer as the belt is moved and stretched as, for example, during wear. Apertures in a layer will open, close, change shape and shift relative the other layer, providing a visual impression of complexity, depth and added texture. Apertures with various shapes, and angles relative the machine direction, can result in z-direction projections and/or ridges along the edges of the apertures when the belt structure contracts. Referring to FIG. 7C, for example, when the belt structure contracts in either the lateral or longitudinal direction, "flaps" created by the depicted aperture 41 shapes may stand up and add z-direction loft in addition to the height of the rugosities. The added loft may contribute to tactile and visual perceptions of added softness and/or breathability. Additionally, with expansion and contraction of the belt structure the "flaps" may open and close, alternately revealing and concealing any contrasting appearance and/or color of the underlying layer, and giving the belt structure a more complex and lively appearance.

It may be appreciated that the pattern of apertures selected may be coordinated with the pattern of adhesive selected to adhere the laminate, for varying effects. Referring to FIG. 8A, for example, a pattern of apertures may be selected that is somewhat independent of the pattern of rugosities created by a pattern of adhesive. The adhesive pattern may be selected so as to provide, for example, orderly machine direction rows but disordered or random cross direction columns of rugosities 27. The pattern of apertures 41 may be sized and ordered so as to fall randomly on the rugosities 27 in the machine and/or cross directions. As a result, the apertures will be positioned relative the rugosities in a somewhat random fashion, providing a particular visual effect. In another example illustrated in FIG. 8B, the pattern of adhesive may be selected to provide substantially orderly machine direction rows and cross-direction columns of rugosities. The apertures 41 may be patterned, for example, so as to cause them to fall on the peaks 28 of the rugosities 27, in, for example, substantially evenly-spaced rows and substantially evenly-distributed numbers. In this latter example, the apertures are positioned substantially at the peaks 28 of the rugosities 27 at a location on the nonwoven web layer at which they will experience the most movement (having another visual effect), as the belt is stretched and moved, as during wear of the article. Similarly, the apertures may be patterned in coordination with the spacing between the elastic members such as strands 26, such that they are substantially evenly distributed relative the locations of the strands 26 in the belt. For example, a pattern of apertures may have an aperture spacing ASC along the cross direction that is a substantially even multiple or substantially even divisor of the elastic band spacing ESC in the cross direction in any given portion, or even the entirety, of the belt. Similarly, a pattern of apertures may have an aperture spacing ASM along the machine direction that is a substantially even multiple or substantially even divisor of the rugosity spacing RSM in the machine direction in any given portion, or even the entirety, of the belt. In the example of FIG. 8B, RSM≈ASM, so each divides into the other substantially evenly by 1. In the same example, ESC≈3 ASC, so ESC divides substantially evenly into ASC by 3. FIG. 8C depicts another example wherein the pattern of adhesive deposits is configured to produce rugosities 27 with peaks 28 and valleys 29 that are substantially continuous along the cross direction (i.e., having few or no interruptions at the elastic strands 26 or elsewhere); this may be accomplished by a pattern of substantially continuous, linear deposits of adhesive between layers 24, 25 along the cross direction. In FIG. 8C, again, the pattern of apertures may be configured such that the aperture spacing ASM along the machine direction is a substantially even multiple or substantially even divisor of the rugosity spacing RSM in the machine direction.

The visual effects of an apertured nonwoven layer in a belt may be multiplied if both layers 24, 25 are apertured. In the event aperturing of both layers 24, 25 is desired, however, it may be desirable that that the apertures of the respective layers 24, 25 are offset relative each other, in other words, that they do not align when the material is stretched against elastic-induced contraction to pull out the rugosities. This may be deemed important to avoid giving the belt a ragged appearance, or to avoid portions of the wearer's skin showing through the belt, or both. For this reason, it may be desired that the spacing of the aperture patterns in the respective layers differ. Alternatively, where substantially identical aperture patterns are present in both layers, it may be desired that the patterns are not in phase with each other in either or both the machine direction and cross direction, when the belt is stretched against elastic-induced contraction to pull out the rugosities.

The visual effects of an apertured nonwoven layer in a belt may be enhanced if the material of one layer has a color that visually contrasts with the color of the other layer. The material of one or both layers may be tinted, pigmented or printed in one or more colors or shades (including white) such that the colors or shades of the respective layers visually contrast. The contrasting color or shade of one layer can then be seen through apertures of the other layer for interesting visual effect. Herein, a "visual contrast" between colors or shades of two respective layers of material means that the value of delta E* determined through the Visual Contrast method below is equal to or greater than 2.0. For enhanced visual contrast, it may be preferred that the value of delta E* be equal to or greater than 3.5.

Nonwoven web materials of the type typically used to form such belts are generally highly breathable. (Breathability, typically reflected in measurable vapor permeability of the material, is desired to avoid overhydration of the wearer's skin beneath the article.) Accordingly, it not necessary or desirable to provide apertures merely for the purpose of increasing breathability. Because the materials are already highly breathable aperturing may have little effect in this regard. However, it is believed that the visible presence of apertures in the material may in some circumstances give consumers the impression of high breathability, or reinforce or increase such impression—which may provide a marketing advantage for the manufacturer.

Visual Contrast

The color difference measurement is based on the CIE L*a*b* color system (CIELAB). A flat bed scanner capable of scanning a minimum of 24 bit color at 1200 dpi and has manual control of color management (a suitable scanner is an Epson Perfection V750 Pro from Epson America Inc., Long Beach Calif.) is used to acquire images. The scanner is calibrated against a color reflection target compliant to ANSI method IT8.7/2-1993 using color management software (a suitable package is MonacoEZColor available from X-Rite Grand Rapids, Mich.) to construct a scanner profile. The resulting calibrated scanner profile is opened within an imaging program that supports sampling in CIE L*a*b* (a suitable program is Photoshop S4 available from Adobe Systems Inc., San Jose, Calif.) to measure bonded and unbonded areas.

Turn on the scanner for 30 minutes prior to calibration. Place the IT8 target face down onto the scanner glass and close the scanner lid. Open the MonacoEZColor software and select acquire image using the Twain software included with the scanner. Within the Twain software deselect the unsharp mask setting and any automatic color correction or color management options that may be included in the software. If the automatic color management cannot be disabled, the scanner is not appropriate for this application. Acquire a preview scan at 200 dpi and 24 bit color. Insure that the scanned image is straight and first outer surface facing side-up. Crop the image to the edge of the target, excluding all white space around the target, and acquire the final image. The MonacoEZColor software uses this image to compare with included reference files to create and export a calibrated color profile compatible with Photoshop. After the profile is created the scan resolution (dpi) can be changed, but all other settings must be kept constant while imaging samples.

Provide respective samples of each layer 75 mm by 75 mm square. Precondition the samples at about 23° C.±2° C. and about 50%±2% relative humidity for 2 hours prior to testing.

Open the scanner lid and place the first sample onto the scanner glass with the first outer surface facing the glass. Cover the sample with the white background (in this test method white is defined as having L*>94, −2<a*<2, and −2<b*<2) and close the lid. Acquire and import a scan of the first sample into Photoshop at 600 dpi and 24 bit color. Assign the calibrated scanner profile to the image and change the mode to Lab Color ("Lab Color" in Photoshop corresponds to the CIE L*a*b* standard). Select the "eyedropper" color selection tool. Set the sampling size of the tool to include as many pixels as possible within an area of the sample 2 mm by 2 mm square, which does not include an aperture. Using the eyedropper tool measure and record L*a*b* values in 10 different 2 mm by 2 mm square areas (not having apertures) in the sample image. Average the 10 individual L*a*b* values and record as $L_1$, $a_1$, and $b_1$ respectively.

Repeat the steps in the paragraph above for the second sample, and record the averaged values as $L_2$, $a_2$ and $b_2$. Calculate and report the color difference (delta E*) between the bonded and unbonded areas using the following equation:

$$\text{delta } E^* = \sqrt{(L_2^* - L_1^*)^2 + (a_2^* - a_1^*)^2 + (b_2^* - b_1^*)^2}$$

and report to the nearest 0.01 units. A total of three substantially identical samples of each layer are measured for each sample set. Average the three delta E* values and report to the nearest 0.1 unit.

\* \* \*

All patents and patent applications (including any patents which issue thereon) referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended that the scope of the invention is limited only by the appended claims and equivalents thereof.

What is claimed is:

1. A textured laminate structure, comprising:
   a first layer formed of a first nonwoven web having a machine direction, the first nonwoven web being formed of polymeric fibers having a machine direction bias and having a pattern of pre-bonds thereon, and a first preexisting pattern of first apertures therethrough;
   a second layer; and
   a plurality of spaced apart strands of elastomeric material oriented along the machine direction, disposed between the first layer and the second layer and bonded therebetween, the strands of elastomeric material having been disposed between the first and second layers in a pre-strained condition, thereby forming a pattern of rugosities extending in the z-direction present in at least the first layer when the laminate is in a relaxed condition,
   wherein the laminate structure is discontinuously joined or bonded such that the first layer is joined or bonded to the structure in first portions of the first layer and unjoined or unbonded to the structure in second portions of the first layer.

2. The laminate structure of claim 1, wherein the rugosities have a machine direction spacing and a cross direction spacing, and the first apertures have a machine direction spacing and a cross direction spacing, and either or both of the following relationships exist in at least a portion of the laminate structure:
   a) the machine direction rugosity spacing is a substantially even divisor or substantially even multiple of the machine direction first aperture spacing;
   b) the cross direction rugosity spacing is a substantially even divisor or substantially even multiple of the cross direction first aperture spacing.

3. The laminate structure of claim 1, wherein the strands have a cross direction spacing, and the first apertures have a cross direction spacing, and the cross direction strand spacing is a substantially even divisor or substantially even multiple of the cross direction first aperture spacing.

4. The laminate structure of claim 1, wherein the rugosities have a machine direction spacing, and the first apertures have a machine direction spacing, and the machine direction rugosity spacing is a substantially even divisor or substantially even multiple of the machine direction first aperture spacing.

5. The laminate structure of claim 1 wherein the preexisting pattern of first apertures is substantially similar to the pattern of pre-bonds in one or more of: machine-direction spacing, cross-direction spacing, aperture shape and aperture size.

6. The laminate structure of claim 1 wherein the second layer is formed of a second nonwoven web.

7. The laminate structure of claim 6 wherein the second nonwoven web has a second preexisting pattern of second apertures therethrough.

8. The laminate structure of claim 1 wherein a majority of the first apertures define shapes whose greatest dimension is oriented along the machine direction.

9. The laminate structure of claim 1 wherein the first apertures define shapes selected from the group consisting of rod-shaped, arc-shaped, other curved finite paths, oval, elliptical or polygon, and any combinations thereof.

10. The laminate structure of claim 1 wherein the first apertures are defined by edges at which the material of the fibers is thermally fused, or deformed and entangled.

11. The laminate structure of claim 1 wherein one of the first or second layers is tinted, pigmented or printed in a first color that visually contrasts with a second color of the other of the first or second layers.

12. The laminate structure of claim 1 wherein the first nonwoven web comprises spunbond fibers formed of polyolefin.

13. The laminate structure of claim 1 wherein the first nonwoven web is a carded material comprising staple fibers.

14. The laminate structure of claim 1 wherein the first layer is bonded to the structure by a pattern of adhesive disposed between the first layer and the second layer.

15. The laminate structure of claim 1 wherein the first layer is bonded to the structure by a pattern of thermal or compression bonds between the first layer and the second layer.

16. The laminate structure of claim 1 wherein the rugosities have peaks, and at least some of the first apertures are present on the peaks.

17. A disposable absorbent article in the form of a pant or diaper having a front waist region ending at a front waist edge, a rear waist region ending at a rear waist edge, the waist edges defining a lateral direction, wherein the laminate structure of claim 1 forms a panel interconnecting the front and rear waist regions.

18. The disposable absorbent article of claim 17 wherein the machine direction is substantially parallel with the lateral direction.

\* \* \* \* \*